United States Patent [19]
Chen et al.

[11] Patent Number: 6,080,160
[45] Date of Patent: Jun. 27, 2000

[54] USE OF SHAPE MEMORY ALLOY FOR INTERNALLY FIXING LIGHT EMITTING DEVICE AT TREATMENT SITE

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 08/760,057

[22] Filed: Dec. 4, 1996

[51] Int. Cl.[7] .................................................. A61B 17/00
[52] U.S. Cl. .................................. 606/72; 606/2; 607/96; 128/897
[58] Field of Search .................................. 606/72, 73, 74, 606/75, 76, 77, 219, 220, 232; 607/88, 96, 115, 116

[56] References Cited

U.S. PATENT DOCUMENTS

| | | | |
|---|---|---|---|
| 3,789,838 | 2/1974 | Fournier et al. | 128/130 |
| 4,427,000 | 1/1984 | Ueda | 600/143 |
| 4,485,816 | 12/1984 | Krumme | 128/334 R |
| 4,665,906 | 5/1987 | Jervis | 606/72 |
| 4,898,156 | 2/1990 | Gatturna et al. | 606/72 |
| 4,935,068 | 6/1990 | Duerig | 148/11.5 C |
| 5,002,563 | 3/1991 | Pyka et al. | 606/222 |
| 5,147,370 | 9/1992 | McNamara et al. | 606/108 |
| 5,171,252 | 12/1992 | Friedland | 606/151 |
| 5,197,978 | 3/1993 | Hess | 606/72 |
| 5,219,358 | 6/1993 | Bendel et al. | 606/222 |
| 5,267,960 | 12/1993 | Hayman et al. | 604/106 |
| 5,290,289 | 3/1994 | Sanders et al. | 606/61 |
| 5,509,923 | 4/1996 | Middleman et al. | 606/207 |
| 5,514,178 | 5/1996 | Torchio | 623/12 |
| 5,522,845 | 6/1996 | Wenstrom, Jr. | 606/232 |
| 5,542,434 | 8/1996 | Imran et al. | 128/772 |
| 5,571,104 | 11/1996 | Li | 606/72 |
| 5,578,074 | 11/1996 | Mirigian | 623/12 |

OTHER PUBLICATIONS

S.M. Andrews et al., "Shape memory alloys in minimally invasive therapy," Minimally Invasive Therapy 1995: 4: 315–318; ©1995 Blackwell Science Ltd.

E. Cingolani et al., "The Two Way Shape Memory Effect In Cu–Zn–Al Single Crystals: Role of Disclocations and Stabilization," *Acta metall. mater.* vol. 43, No. 6, pp. 2451–2461, 1995; © 1995 Elsevier Science Ltd., Printed in Great Britain.

Mitek Surgical Products, Inc. Brochure for *Mitek GII Anchor*™, ©1991 Mitek Surgical Products, Inc., 2 pages.

H. Oonishi et al., "Studies on the Development of a High–Frequency Induction Heating Apparatus to Heat a Shape Memory TiNi Alloy Implanted in a Living Body," *Biomaterials and Biomechanics* 1983, edited by P. Ducheyne et al., Elsevier Science Publishers B.V., Amsterdam, 1984, pp. 155–161.

L. McDonald Schetky, "Shape–Mrmory Alloys," *Sci. Am.*, vol. 241 No. 5, Nov. 1979, pp. 74–83.

*Primary Examiner*—Robert L. Nasser
*Attorney, Agent, or Firm*—Ronald M. Anderson

[57] ABSTRACT

A method and apparatus for selectively engaging and disengaging an anchor to fix a medical device at a selected site within a patient's body. A shape memory alloy (SMA) such as Nitinol is used to fabricate one or more anchors for the medical device. The shape memory effect exhibited by the SMA is thermally activated. One embodiment of the anchor has a substantially circular shape when at its martensite temperature and reverts to an elliptical shape at its austenite temperature. Another embodiment is a substantially straight strip at its martensite temperature and has an end that curls to engage tissue when at its austenite temperature. Still another embodiment includes a pair of anchors that extend outwardly from each side of an elongate probe at their austenite temperature and retract inwardly against the sides of the probe at their martensite temperature. The change in the shape of the SMA elements tends to anchor the medical device or probe at the treatment site. To change the temperature of the SMA elements, an electrical current is selectively energized to provide heat, or thermal conduction between the SMA and a heat source or a heat sink is employed.

43 Claims, 8 Drawing Sheets

USE OF SHAPE MEMORY ALLOY FOR INTERNALLY FIXING LIGHT EMITTING DEVICE AT TREATMENT SITE

FIELD OF THE INVENTION

The present invention generally relates to an apparatus and method for fastening a medical device at a treatment site, and more specifically, to the use of an element that is selectively deployed to anchor the medical device at an internal site within a patient's body.

BACKGROUND OF THE INVENTION

Several different embodiments of light emitting probes for administering photodynamic therapy (PDT) to an internal site within a patient's body are disclosed in commonly assigned U.S. Pat. No. 5,445,608. Further, a number of embodiments of flexible light emitting probes are disclosed in commonly assigned pending U.S. patent application Ser. No. 08/613,390 and a continuation-in-part patent application thereof, Ser. No. 08/633,171, both entitled, "Flexible Microcircuits for Internal Light Therapy." In the above-referenced patent, it is generally contemplated that a probe containing a plurality of light sources can be transcutaneously introduced to a desired treatment site through a surgical incision and then left in place for an extended period of time so that the light emitted by light emitting diodes (LEDs) or other types of light sources included in the probe can effect PDT to destroy abnormal tissue or other types of pathogenic organisms that have absorbed a photodynamic agent. Similarly, the flexible microcircuits of the above-noted pending patent applications are generally intended to be introduced into the body through a natural opening or through a small incision and positioned at the treatment site using conventional endoscopic techniques. These applications teach that a probe may be fixed at a treatment site using sutures, staples, or a biocompatible adhesive.

While any of the techniques that are typically used for attaching a medical device to a site within a patient's body can effectively anchor a rigid or flexible light emitting probe in a desired position, additional time and steps are required for a surgeon to endoscopically affix the device in place after it has been positioned at a treatment site. Even if the treatment site is fully exposed through a surgical procedure, it will typically be necessary to attach the probe at the treatment site before closing the incision. Clearly, it would be desirable to use a mechanism that is selectively deployed from outside the patient's body to fix a probe at a treatment site, without requiring the physician to use sutures, staples, or adhesive.

U.S. Pat. No. 5,267,960 (Hayman et al.) discloses a "Tissue Engaging Catheter for a Radioactive Source Wire," which teaches a selectively deployed anchor comprising two spring loaded, hook-shaped arms positioned at a distal end of a catheter. The catheter is inserted and moved to a desired location within a patient's body; the arms are then slidably advanced distally from within the tubular body of the catheter. Since the ends of the arms are disposed inside the tubular body as it is inserted into the desired location, they are prevented from engaging adjacent tissue. However, when slid outside the tubular body of the catheter, the tips of the arms penetrate slightly into the tissue, anchoring the distal end of the catheter in place. When thus selectively deployed, one of the arms may extend forward and one backward to prevent movement of the catheter in either longitudinal direction, or both arms may extend generally in the same direction. The arms are made of a biologically inert material such as stainless steel. To detach the ends of the arms from the tissue, the outer tubular body of the catheter can be advanced, forcing the arms to slide back inside the tubular structure. The reference also teaches that the structure or plug to which the arms are attached can be rotated about its longitudinal axis to unthread the plug from the inner member of the catheter so that the catheter can be withdrawn from the patient's body, leaving the plug in place. Once the catheter is anchored, a radioactive wire implant can be advanced through the interior of the catheter to provide treatment to the site at which the distal end of the catheter is fixed.

Although U.S. Pat. No. 5,267,960 describes how the hooked arms can be disengaged from the tissue, the technique requires the manual manipulation of the catheter relative to the inner tubing to which the hooked arms are coupled. If the treatment site is disposed in an organ having tissue that is very frangible, such as the liver, it is possible that the mechanical disengagement of the hooked arms will cause damage to the tissue at the site where the fixture was deployed. In addition, the technique disclosed in the above-referenced patent for anchoring the distal end of a catheter to a site is not particularly applicable to attaching a light source probe comprising a sheet on which an array of light sources are deployed to a tissue surface at a treatment site, since once the sheet is deployed, it will likely not be practical to engage or disengage hooks on the sheet in the manner disclosed in the prior art patent reference. Thus, another approach that enables almost any type of medical device to be selectively engaged and disengaged from tissue at a treatment site is required to minimize the time and effort required to affix such a device in place, and then subsequently remove the device from the patient's body.

SUMMARY OF THE INVENTION

In accordance with the present invention, a method is defined for fixing a medical device at a site within a patient's body. The method includes the step of coupling an anchor formed of a shape memory metal to the medical device. The shape memory metal has a first shape associated with a first state and a second shape associated with a second state, and changes from the first state to the second state as a function of temperature. The medical device is inserted into the patient's body so that it is disposed at the site with the shape memory metal in the first state. Next, the temperature of the shape memory metal is changed so that it transitions from the first state to the second state and changes from the first shape to the second shape. The second shape engages tissue within the patient's body so as to resist movement of the medical device relative to the site in at least one direction, and thus tends to fix the medical device at the site. Further, the temperature of the shape memory metal is again changed so that it transitions from the second state to the first state and changes from the second shape to the first shape. After being changed back to the first shape, the shape memory metal disengages from the tissue within the patient's body so as to permit removal of the medical device from the site.

Further, the step of changing temperature is preferably accomplished either by energizing an electrical current to heat the shape memory metal and de-energizing the electrical current to enable the shape memory metal to cool, or by supplying thermal energy to heat the shape memory metal and conducting thermal energy away from the shape memory metal to enable it to cool.

In one preferred embodiment of the invention, the anchor comprises an elastomeric spring element that determines a shape of the medical device in one of the first and second states of the shape memory metal. The shape memory metal determines the shape of the medical device in the other of the first and the second states of the shape memory metal, and the shape of the medical device determines whether the medical device is fixed at the site. There are two different approaches that use the spring element. In the first approach, the shape memory metal changes the shape of the medical device to engage tissue at the site, and the spring element changes the shape of the medical device to disengage the tissue at the site. Alternatively, the spring element changes the shape of the medical device to engage tissue at the site, and the shape memory metal changes the shape of the medical device to disengage the tissue at the site.

As disclosed below, the shape memory metal can be heated to change its temperature by inducing eddy currents to flow within the shape memory metal. An induction coil brought into the proximity of the shape memory coil provides the inductive heating for this embodiment.

Another aspect of the present invention is directed to an apparatus for fixing a medical device at a site within a patient's body. The apparatus includes a shape memory element that is connected to the medical device. The shape memory element has a first shape associated with a first state and a second shape associated with a second state, and changes from the first state to the second state as a function of temperature. Means are provided for heating the shape memory element, causing it to transition from the first state to the second state. One of the first and second shapes is adapted to engage tissue within the patient's body so as to resist movement of the medical device in at least one direction, thus tending to fix the medical device at the site.

In different embodiments of the apparatus, the second shape comprises either an expanded loop, a hook shaped element, or a serpentine shaped element. The first shape comprises a collapsed loop or a substantially straight element. To provide light therapy, the medical device comprises a probe on which a light source is disposed. For example, one embodiment of the medical device includes a substantially planar sheet on which a grid of LEDs are arrayed. A biocompatible coating is preferably applied to the apparatus. Also preferably provided are means for heating the shape memory element, such as a resistive heating element that is energized by an electrical current. Alternatively, a thermal element serves as a heat source or a heat sink of thermal energy, to modify the temperature of the shape memory element.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention uses a shape memory alloy (SMA) to selectively affix a medical device within a patient's body.

As discussed in great detail below, FIGS. 1–18 illustrate various embodiments of the invention. In each embodiment, one or more anchors are remotely activated to engage tissue within the patient's body, and are subsequently selectively disengaged to release the medical device, for example after a medical therapy, such as PDT, has been administered by the medical device. Each of the anchors employs the shape memory effect of the SMA to assist in fixing the probe or releasing the probe from tissue at the treatment site.

SMAs are a family of alloys having anthropomorphic qualities of memory and trainability. These alloys possess attributes that make them especially useful for anchoring a medical device, such as a light emitting probe, within a patient's body as discussed in detail below. A particularly useful attribute of an SMA is that when it is plastically deformed at a particular temperature, it can completely recover its original shape on being raised to a higher predefined temperature. In recovering its original shape, the SMA produces a powerful displacement force that is approximately 200 times greater than a force produced by the expansion and contraction of a bimetallic element of the same weight. Moreover, a particular SMA can be selected so that the shape memory effect occurs at a predetermined desired temperature that is sufficiently low so as to cause minimal damage to any adjacent tissue in the patient's body. To produce an SMA element that has a desired single memory shape, the SMA is formed into the desired shape and heated to a temperature so that the crystalline temperature of the SMA is entirely in the beta or austenite phase. The SMA element is then cooled below a defined and characteristic temperature $M_f$ at which the austenite crystal structure of the alloy changes to a martensite crystal structure. The SMA element can then be plastically deformed into a different shape. If the SMA element is then heated above another defined temperature $A_f$ (where $A_f > M_f$) at which the martensite crystalline structure of the alloy is again converted to the austenite crystalline structure, the SMA moves and exerts force as it changes back into the memory shape. This process can be repeated indefinitely, with the same results.

In 1962, an SMA of nickel and titanium (referred to as "Nitinol") was discovered. Nitinol alloy is an SMA that can retain shape memories for two different physical configurations of the alloy, at two different temperatures through a process of trainability. The training of a Nitinol alloy (and other SMAs) for two different shape memory configurations is generally accomplished by limiting the number of variants of martensite formed when an alloy is repeatedly heated above and then cooled below the critical temperature $M_f$. To train the allow to two different memory shapes, a five step sequence is implemented, as follows: (1) the alloy's temperature is raised to above the beta (austenite) phase temperature while the alloy is maintained in a first shape; (2) the shaped alloy is quenched or quickly cooled to a lower temperature at which the austenite crystals break apart and new martensite crystals start to form in the alloy's molecular structure; (3) while cool, the element is plastically deformed into a second shape, applying stress that tends to favor one variant of martensite crystalline structure over another; (4) the element is then heated to the beta phase after being reformed into the first shape; and, (5) the previous four steps are repeated until the first and second shapes spontaneously occur in the alloy, respectively, when austenite and martensite crystals form in the molecular structure of the alloy at the temperatures $A_f$ and $M_f$, respectively.

The temperature at which a shape is "memorized" by an SMA is thus a function of the temperatures at which martensite and austenite crystals form in that particular alloy. Further, crystal formation temperatures are a function of the metallic composition of the particular alloy used and any stresses applied during the crystal formation process. The Nitinol family of alloys can be fabricated so that the shape memory effect will occur at any point over a range of −270° to +100° Celsius. However, it is contemplated that the present invention can also be fabricated using SMAs that are substantially different in composition than Nitinol. Recently, a new family of SMAs based on copper, zinc and aluminum was developed. These alloys have a range of crystal formation temperatures that are similar to Nitinol, and shape memory training of the new alloys is performed in substantially the same manner as discussed above.

The selection of a particular SMA to anchor a medical device requires the careful consideration of several parameters: (1) metallic composition of the alloy; (2) the austenite and martensite crystal formation temperatures; (3) the stresses that may be applied during crystal formation; and (4) the amount of force and deflection required of the anchor.

One embodiment of an anchor 110 is shown in FIGS. 1–5. Anchor 110 is used to fix the position of a medical device 108 within a patient's body, minimizing displacement of the medical device from a treatment site 100 due to movement of the patient and of adjacent tissue structure. The medical device may, for example, comprise a plurality of light sources (not separately shown) arrayed around the circumference of the device, for use in providing light therapy to the treatment site; however, other types of medical devices can also be fixed at the treatment site using the present invention.

Figure 1:
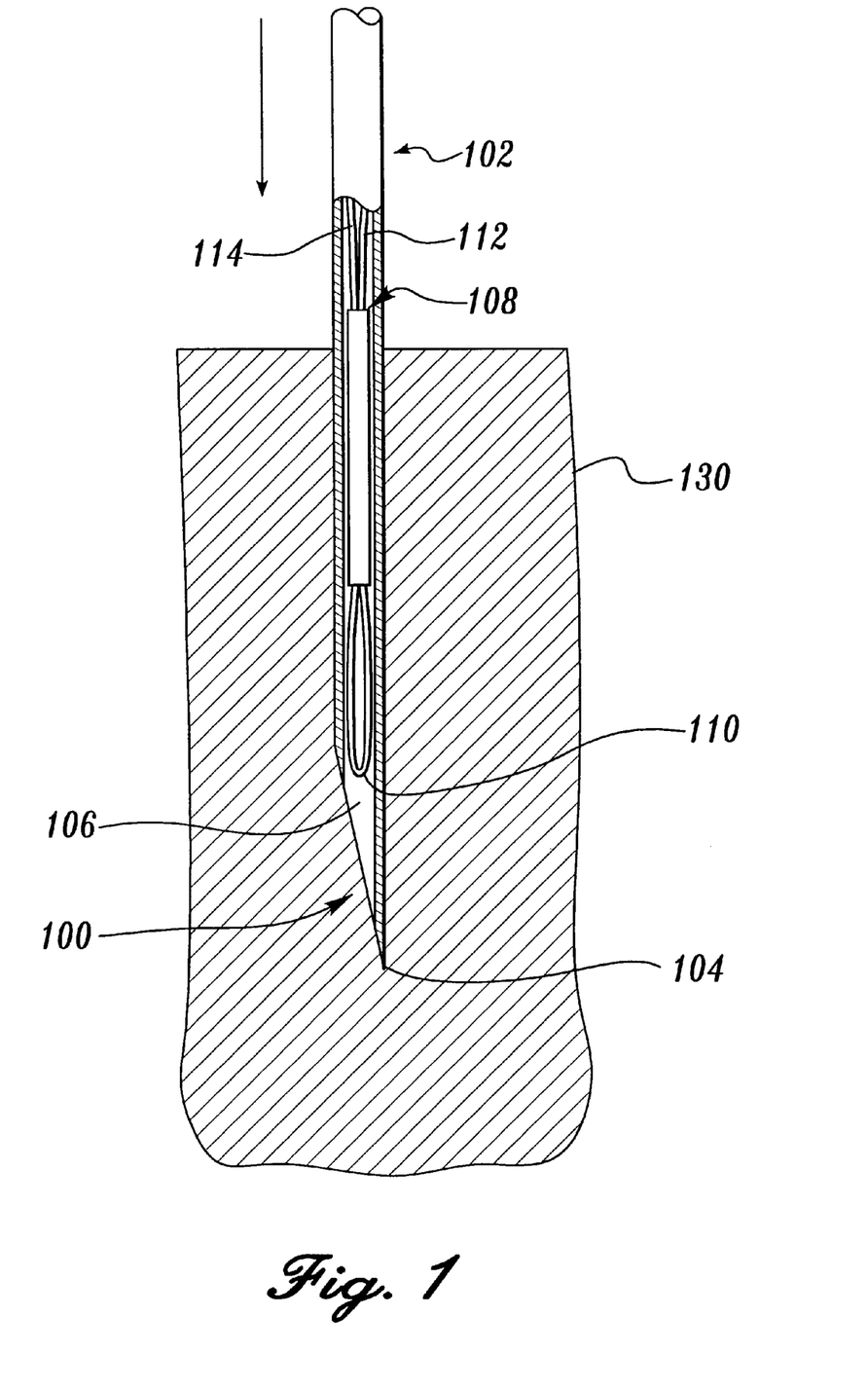
FIG. 1 is a side-sectional view of a catheter containing a medical device with an anchor in accord with the present invention, showing the medical device being inserted into a patient's tissue.

As shown in FIG. 1, a catheter 102 has a lumen 106 in which medical device 108 is delivered to treatment site 100 within tissue 130. Catheter 102 is shown after it has been inserted into tissue 130, which may be cutaneous or subcutaneous tissue, part of an organ, or a portion of a tumor disposed within a patient's body. The catheter has a sharpened tip 104 so that it can be directly inserted into soft tissue, without requiring an incision. Depending upon the location of treatment site 100, the catheter may be advanced into the patient's body toward the treatment site using conventional endoscopic techniques, or may be inserted directly into the patient's body and into the treatment site through the epidermis.

Figure 2:
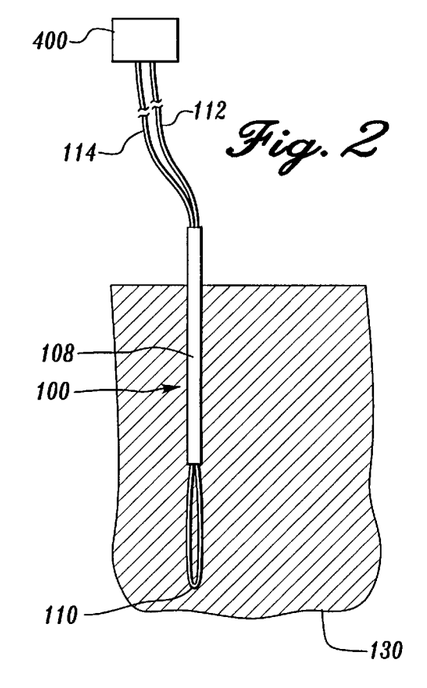
FIG. 2 is a side view of the medical device and anchor of FIG. 1 disposed within the patient's tissue and showing the anchor, which has a generally closed loop shape, prior to it's activation to affix the medical device at a treatment site.
Figure 3:
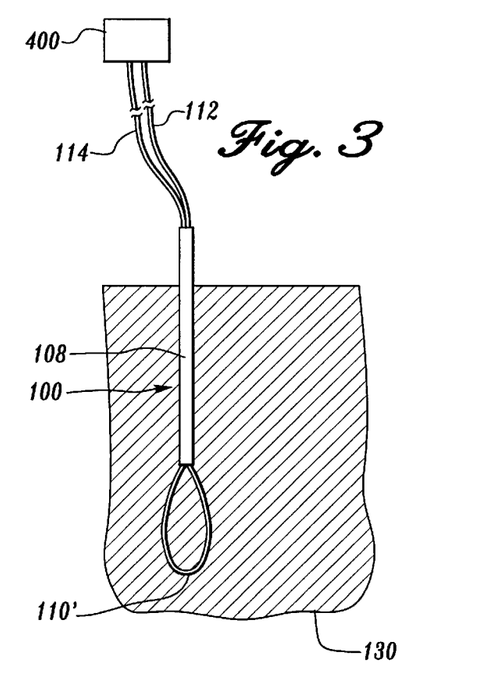
FIG. 3 is a side view of the anchor of FIGS. 1 and 2 after it has activated to affix the medical device at the treatment site, by expanding to a larger diameter loop.

In FIG. 2, catheter 102 has been retracted, after depositing medical device 108 and anchor 110 within tissue 130. Anchor 110 is coupled to a distal end of medical device 108, a first lead 112 and a second lead 114 extending from the proximal end of the medical device. As noted above, anchor 110 is fabricated from an SMA selected for its specific phase change temperature characteristics and other parameters such as restoring force. When initially deployed at treatment site 100, anchor 110 has a generally elliptical shape, appearing as a collapsed loop with a relatively small cross section. In FIG. 3, the anchor is shown after it has been activated (and as such, is now referred to by reference number 110') to anchor medical device 108 in tissue 130 at treatment site 100. The steps involved in selectively activating the anchor to change shape from the collapsed loop shape of anchor 100 to the open loop shape of anchor 110' are discussed below.

Figure 4:
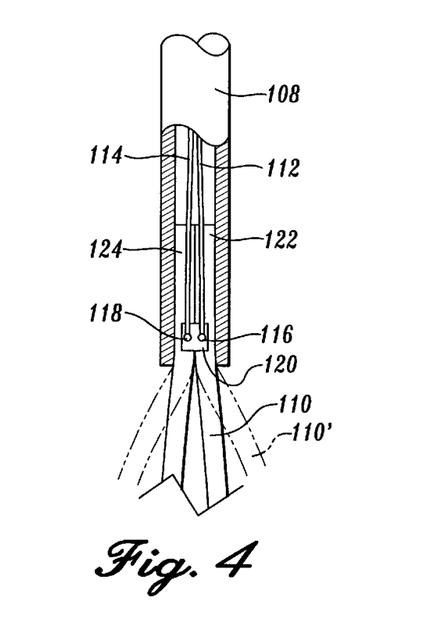
FIG. 4 is a side-sectional view of an electrical connection to the anchor of FIGS. 1 through 4, showing an electrically conductive metal plate attached to the ends of the loop.

Referring now to FIG. 4, a side cross sectional view of medical device 108 prominently illustrates electrical connections for anchor 110/110'. First lead 112 and second lead 114 are attached, respectively, by a connection 116 and a connection 118 to a heater plate 120. The other ends of first lead 112 and second lead 116 are electrically coupled to a power supply 400 that is remotely located, preferably at another internal site within the patient's body. Heater plate 120 is fabricated of an electrically and thermally conductive material whose temperature proportionally increases with the flow of electrical current through the plate. Further, heater plate 120 is mechanically attached, e.g., by an appropriate adhesive, to a first end 122 and a second end 124 of anchor 110/110' so that heat produced by heater plate 120 is directly conducted to anchor 110/110'.

A user of the present invention selectively activates or engages and disengages anchor 110/110' in the following manner. Heat is applied to anchor 110 from heater plate 120 when an electrical current is conveyed from power supply 400 through first lead 112 and second lead 114. The flow of electrical current through heater plate 120 causes a resistive heating of the heater plate that substantially increases its temperature. The elevated temperature of heater plate 120 causes the temperature of anchor 110 to increase. As the temperature of anchor 110 increases above its austenite phase change temperature, austenite crystals form in the molecular structure of the SMA comprising the anchor. Once austenite crystals start to form, the shape memory effect causes the shape of the anchor to change to the open loop of anchor 110', securely fixing the anchor and attached medical device 108 at treatment site 100 within tissue 130. After the user interrupts the flow of electrical current through heater plate 120, anchor 110' begins to cool, which causes the austenite crystals to break down and reform as martensite crystals. At the onset of martensite crystal formation, the shape memory effect causes anchor 110' to rapidly revert to the closed loop shape of anchor 110, so that the anchor and attached medical device 108 can readily be removed from the patient's body.

Figure 5:
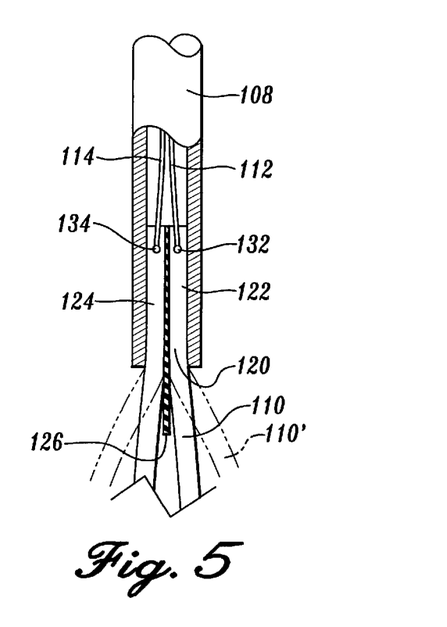
FIG. 5 is a side-sectional view of the anchor of FIGS. 1 through 4, showing an electrical connection to the loop with an insulator disposed between the ends of the loop.

Looking now to FIG. 5, an alternative approach is illustrated for activating a shape memory change in anchor 110. In this approach, first lead 112 and second lead 114 are directly attached to anchor 110/110' by a connection 132 on first end 122 and by a connection 134 on second end 124 of the anchor. Also, the two ends of the anchor are separated by an electrical insulator 126 to ensure that the electrical current flows through the anchor 110 before returning to power supply 400. The Nitinol alloy (or other SMA) that comprises loop 110 is both electrically and thermally conductive so that its temperature increases due to resistive heating caused by the flow of electrical current through the anchor.

A user of the alternative embodiment of positioner 100 engages and disengages the device as follows. A temperature increase of anchor 110 is caused by selectively enabling an electrical current from power supply 400 to flow through first lead 112 and second lead 114, which are connected to the ends of anchor 110. As the electrical current flows through the anchor, its temperature increases sufficiently so that austenite crystals begin to form in the molecular structure of the SMA comprising the anchor. At the onset of austenite crystal formation, the shape memory effect swiftly causes a change from the collapsed loop shape of anchor 110 to the engaged open loop shape of anchor 110', and medical device 108 is anchored within the patient's body at the treatment site. After the user interrupts the flow of electrical current through anchor 110', it cools and the austenite crystals begin to break apart as martensite crystals start to form. At the onset of martensite crystal formation, the shape memory effect causes anchor 110' to rapidly return to the collapsed loop shape of anchor 110, enabling the medical device and anchor to be readily removed from tissue 130.

Figure 18:
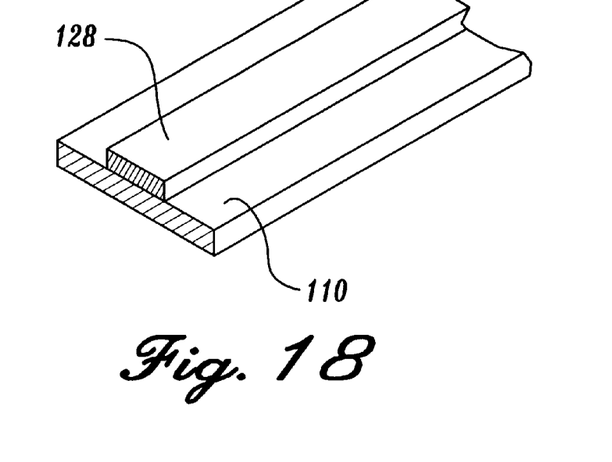
FIG. 18 is an isometric view of a portion of an anchor having a conductive ribbon extending along its surface.

The austenite and martensite crystal formation temperatures of the SMA used to fabricate anchor 110/110' must be within a range that will not harm tissue around treatment site 100. A problem arises when an SMA that is selected for its desirable crystal formation temperatures, has poor electrical and/or thermal conductive properties. Typically, to overcome poor conductivity, the voltage applied to a conductor is simply increased; however, this solution may pose a risk to the patient if too high a voltage is applied. To overcome this constraint, a conductive ribbon 128 may be applied to the surface of anchor 110 as shown in FIG. 18. Ribbon 128 should be fabricated in a width and thickness that determines its resistance and current carrying capability. It is contemplated that ribbon 128 be selected from known conductive materials such as aluminum, copper, gold, silver, and other metals and alloys thereof, or of conductive polymers. Further, electrical current can flow through ribbon 128 in series with anchor 110, or if ribbon 128 is electrically insulated from anchor 110, in parallel therewith. The heat generated in ribbon 128 by the flow of electrical current is directly transmitted to loop 110 by conduction. Since the conductive properties of ribbon 128 can be adjusted to achieve the required austenite and martensite crystal formation temperatures of anchor 110/110', an SMA can be selected for use in fabricating the anchor from a wider range of SMAs.

Anchor 110 may also include a coating (not shown) that has the ability to insulate tissue 130 from the temperature of anchor 110 (and ribbon 128—if used). It should be noted that Nitinol is generally biologically inert. However, it may be desirable to provide a biologically inert coating around medical device 108 and anchor 110/110'. Such a coating would also provide any required thermal insulation to protect tissue 130 from damage due to the elevated temperature of anchor 110/110' when the anchor is heated to the austenite crystal formation temperature.

Figure 6:
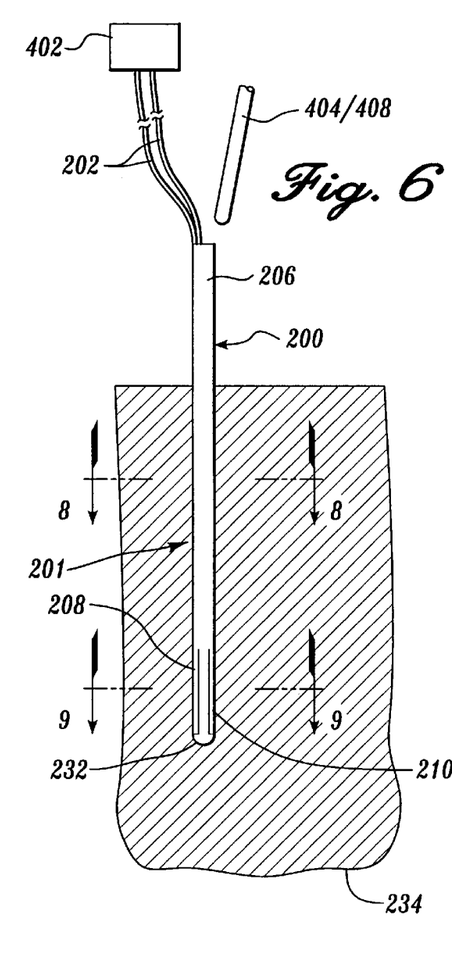
FIG. 6 is a side view of an elongate probe having a pair of selectively extensible anchors in a disengaged position.
Figure 7:
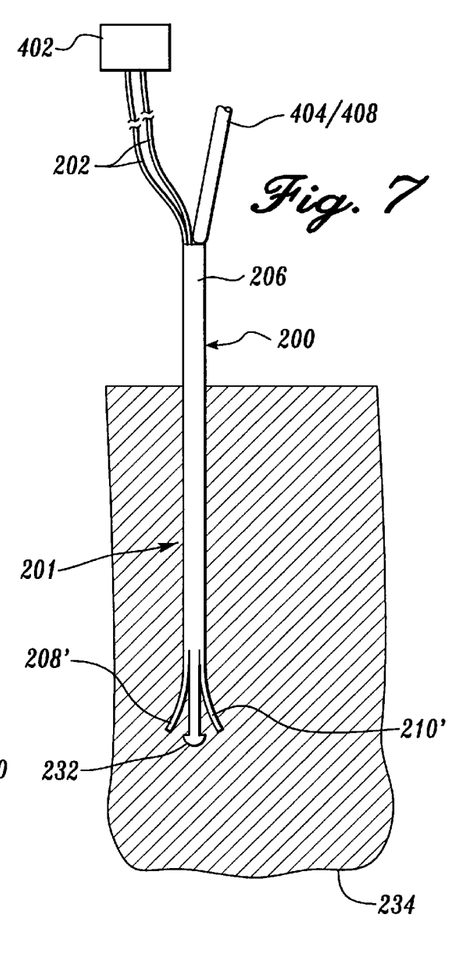
FIG. 7 is a side view of the probe of FIG. 6, showing the pair of extensible anchors in an engaged position.

A second embodiment of the present invention is displayed in FIGS. 6–11 and illustrates the deployment and fixing of a light emitting probe 200 at a treatment site 201 within a patient's body. In FIG. 6, probe 200 is shown after it has been inserted within a tissue 234 of the patient, but before first and second anchors 208 and 210 have been deployed to fix the position of the probe. Probe 200 has a rounded tip 232 disposed adjacent distal ends of first and second anchors 208 and 210. In the disengaged position, the anchors are substantially straight and generally aligned with a longitudinal axis of probe 200. Also, an electrical lead 202 is shown coupled to a light source power supply 402. In FIG. 7, probe 200 is shown after both the first and second anchors have been selectively actuated to engage tissue 234. Once activated to change shape, the first and second anchors are respectively identified by reference numerals 208' 210'. In the engaged position, the anchors extend outwardly from the surface of the probe and have a substantially hooked shape so that probe 200 is securely fixed within the patient's body.

Figure 8:
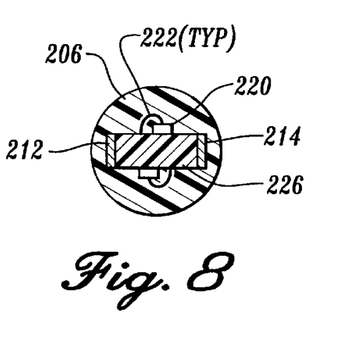
FIG. 8 is a cross sectional view of a top portion of the probe of FIGS. 6 and 7.

Referring now to FIG. 8, a cross sectional view of the upper portion of probe 200 prominently illustrates an upper body 206, a substrate 226 on which are disposed a plurality of light sources 220, a first thermal strip 212, a second thermal strip 214, and a fly wire 222 coupling the light source to a conductive trace (not separately shown) on the substrate. In the preferred embodiment, the light sources comprise light emitting diodes (LEDs), but other types of light sources can also be used. These light sources are mounted on both sides of the substrate in spaced-apart array. Electrical power is supplied to light sources 220 through the conductive traces formed on substrate 226.

Figure 9:
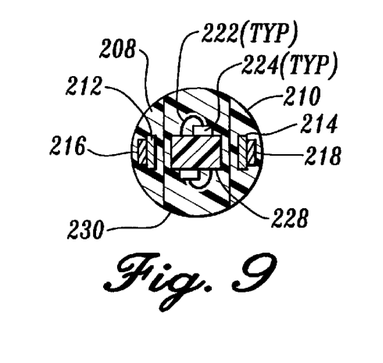
FIG. 9 is a cross sectional view of a bottom portion of the probe of FIGS. 6 through 8, in the portion of the probe in which the extensible anchors are disposed.

With reference to FIG. 9, a cross sectional view of the lower portion of probe 200 illustrates first thermal strip 212, second thermal strip 214, fly wires 222, light sources 224, a first SMA strip 216, a second SMA strip 218, a first anchor 208, a second anchor 210, a lower body 230, and a lower substrate 228. Further, first SMA strip 216 is positioned between first anchor 208 and first thermal strip 212 and second SMA strip 218 is similarly positioned between second anchor 210 and second thermal strip 214. In this configuration, first anchor 208 and second anchor 210 are forced to follow any shape memory deflection by first SMA strip 216 and second SMA strip 218, respectively. First thermal strip 212 and second thermal strip 214 are thermal conductors that convey thermal energy to the SMA strips and a thermal source 404 or a thermal sink 408 that is applied to the proximal (upper) ends of first and second thermal strips 212 and 214.

Figure 10:
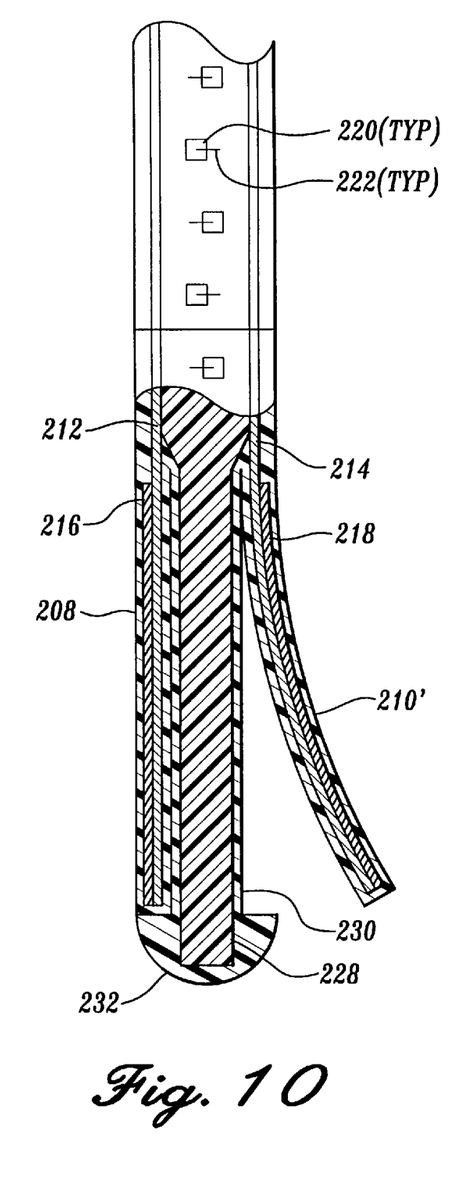
FIG. 10 is a side and sectional view of the probe of FIGS. 6–9, displaying the body encasing the pair of thermal strips, the pair of SMA strips, the LEDs, and the pair of extensible anchors.
Figure 11:
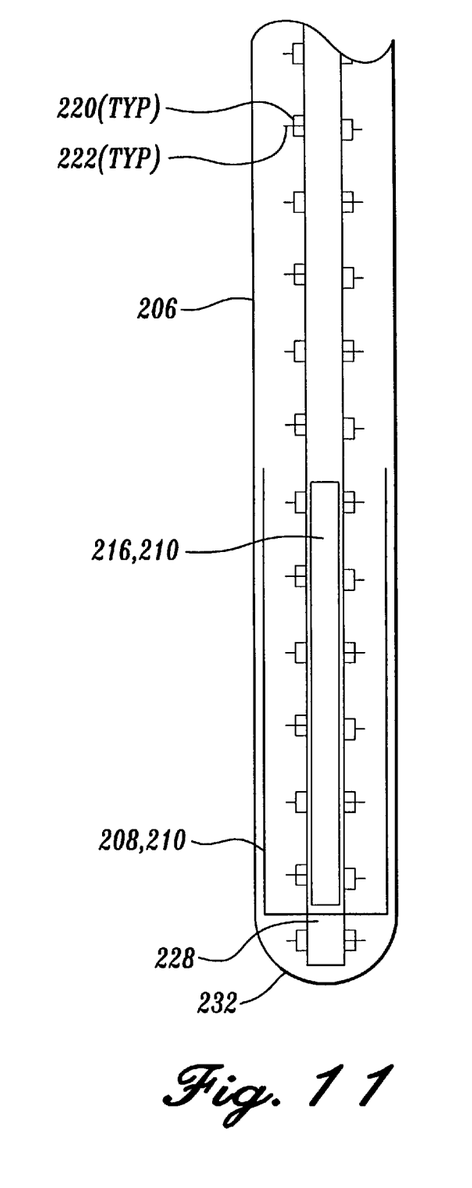
FIG. 11 is another side view of the probe of FIGS. 6 through 10, taken approximately 90° around the longitudinal axis of the probe relative to the view of FIG. 10.

FIG. 10 illustrates probe 200 with second anchor 210' in the engaged position and first anchor 208 in the disengaged position. In FIG. 11, probe 200 is illustrated with anchors 208 and 210 in the disengaged position. Upper body 206 and lower body 230 are fabricated of a material such as a biocompatible plastic polymer that is sufficiently transparent to allow light emitted from light sources 220 to pass through the material and irradiate tissue within the patient's body.

A user selectively actuates first and second anchors 208 and 210 to fix probe 200 in position at the treatment site by transferring thermal energy (heat) from thermal source 404 into first SMA strip 216 and second SMA strip 218. As the temperature of the SMA strips rises, austenite crystals begin to form in the molecular structure of the SMA strips. At the onset of austenite crystal formation, the shape memory effect causes first SMA strip 216 and second SMA strip 218 to quickly deflect outwardly away from the lower body of probe 200, forcing the first anchor and second anchors to their engaged positions identified (first and second anchors 208', 210') so that probe 200 becomes securely fixed within the patient's body. Further, first anchor 208' and second anchor 210' remain in their engaged positions. Next, the user causes electricity to flow from light source power supply 402 to light sources 220 so that tissue 234 is illuminated.

After PDT of tissue 234 is complete, the flow of electricity from light source power supply 402 is interrupted. First SMA strip 216 and second SMA strip 218 are then cooled by applying heat sink 408 to the distal ends of thermal strips 212 and 214. The heat sink can be simply a metal rod that is cooled to a temperature below the martensite temperature of the SMA, which is also below the patient's body temperature, by immersion in a chilled liquid, or may be actively cooled by an expanding compressed fluid flowing through internal passages within the heat sink. As the SMA strips cool, the austenite crystals will start to break apart and martensite crystals will begin forming in the molecular structure of the SMA strips. At a sufficiently low temperature, martensite crystals will form and the shape memory effect will cause the SMA strips to rapidly straighten. As first SMA strip 216 and second SMA strip 218 straighten, they pull first anchor 208' and second anchor 210' to their disengaged positions (characterizing first and second anchors 208 and 210).

Figures 12, 13, 14, 15:
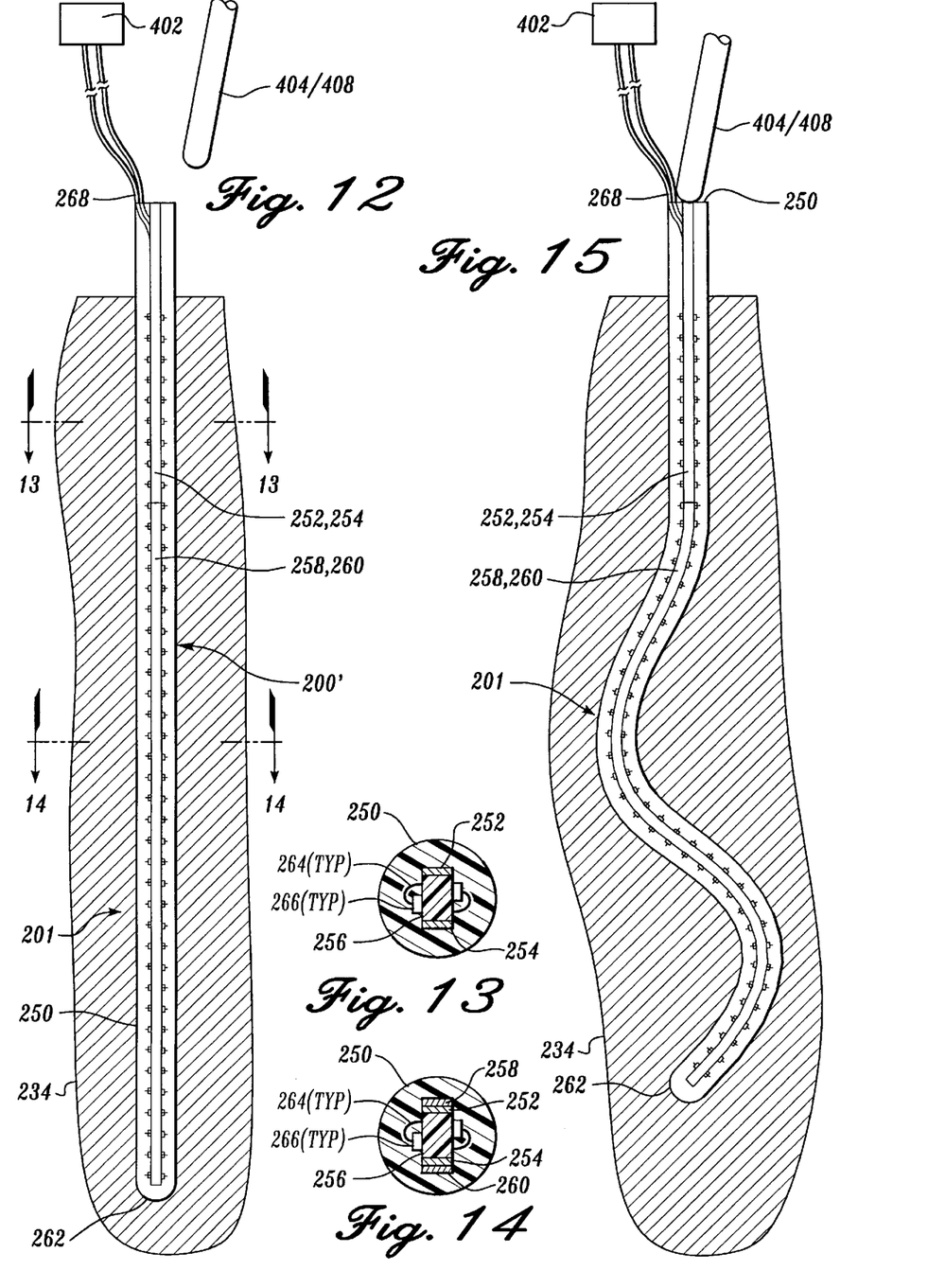
FIG. 12 is a side view of another embodiment of a longitudinal probe prior to activating an anchor to fix the probe within a patient's body.
FIG. 13 is a cross sectional view of a top portion of the probe of FIG. 12.
FIG. 14 is cross sectional view of a bottom portion of the probe of FIGS. 12 and 13, wherein a shape memory metal strip is disposed.
FIG. 15 is a side view of the probe of FIGS. 12 through 14, showing the shape of the probe after the anchor is activated to fix the probe at a treatment site.

An alternative embodiment of the light emitting probe 200' is shown in FIGS. 12–15. In FIG. 12, a probe 200' is illustrated after it has been inserted within tissue 234 of a patient to provide light therapy to treatment site 201. The distal end of probe 200' includes a rounded tip 262, which eases its insertion into the tissue. When initially inserted into the tissue, probe 200' has a substantially straight shape. As shown in FIG. 13, the top portion of probe 200' has a polymeric, elastomeric, and optically transparent body 250 within which are disposed a first thermal strip 252, a second thermal strip 254. The first and second thermal strips extend along opposite edges of a flexible substrate 256, on which are mounted a plurality of light sources 266. A lead 264 couples a flexible conductive trace (not shown) on the substrate to each light source to supply an electrical current to the light source and the light sources are each mounted in electrical contact with another flexible conductive trace (not shown) that extends the length of the substrate. The conductive traces on the substrate are electrically coupled to a lead 268 that is connected to light source power supply 402.

As shown in FIG. 14, first thermal strip 252, second thermal strip 254, and substrate 256 also extend longitudinally through the lower portion of probe 200', within body 250. However, the lower portion also includes a first SMA strip 258 and a second SMA strip 260 that are respectively disposed adjacent to and in contact with first and second thermal strips 252 and 254. The first and second SMA strips extend through approximately the lower three-fourths of the length of probe 200'. FIG. 15 illustrates probe 200' after first and second SMA strips 258 and 260 have been activated by heat transfer from/to a thermal source/sink so that they experience a change in shape. The force exerted by the first and second SMA strips during this change in shape is sufficient to change the shape of probe 200' so that it has a substantially serpentine shape. The serpentine shape of probe 200' shown in FIG. 15 fixes the probe at treatment site 201, generally making it difficult to withdraw the probe from tissue 234.

The activation of first and second SMA strips 258 and 260 is accomplished in a manner substantially similar to that used to activate first and second SMA strips 216 and 218 in the embodiment of probe 200 shown in FIG. 10. Thermal energy is transferred by conduction from thermal source 404 through first thermal strip 252 and second thermal strip 254, respectively, to first SMA strip 258 and second SMA strip 260. Austenite crystals begin to form in the molecular structure of the SMA strips and the shape memory effect rapidly forces them to assume a serpentine shape so that the body of probe 200' engages tissue 234. After probe 200' is fixed at treatment site 201, an electrical current is enabled to flow from light source power supply 402 to light sources 266, so that tissue 234 at the treatment site is illuminated.

After PDT is complete, the user interrupts the flow of electrical current from light source power supply 402. To disengage probe 200' from tissue 234, thermal heat sink 408 is applied to the proximal ends of first and second thermal strips 252 and 254 to conduct heat away from first and second SMA strips 258 and 260 sufficiently so that the austenite crystals start to break down as the molecular structure begins to change into martensite crystals. At the martensite crystal formation temperature, the shape memory effect quickly forces the SMA strips to assume a substantially straight shape so that body 250 of probe 200' also straightens, enabling the probe to be withdrawn from tissue 234.

Figure 16:
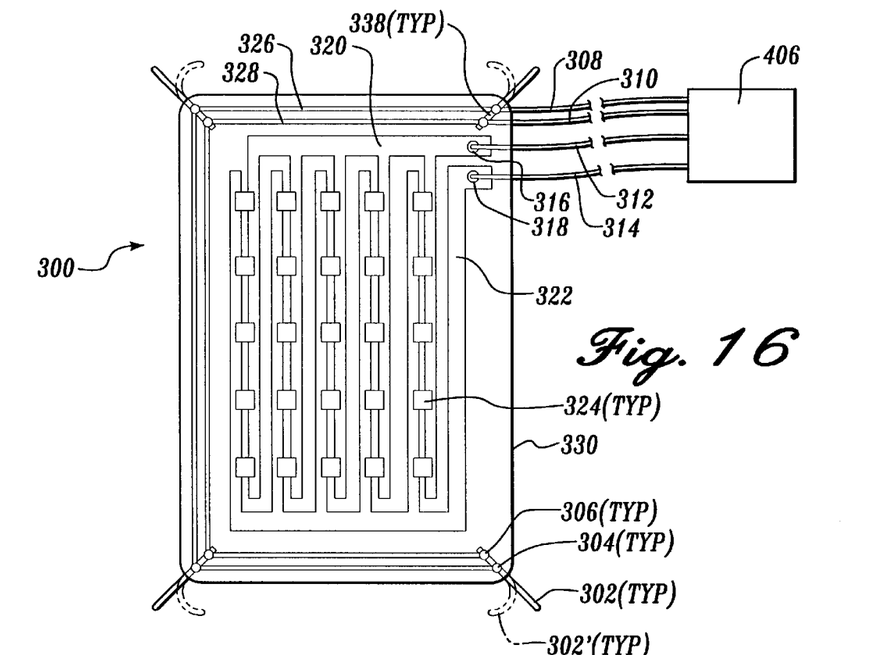
FIG. 16 is a plan view of a quadrilateral sheet-like probe that has four anchors disposed at its corners, each anchor including a segment through which an electrical current selectively flows.
Figure 17:
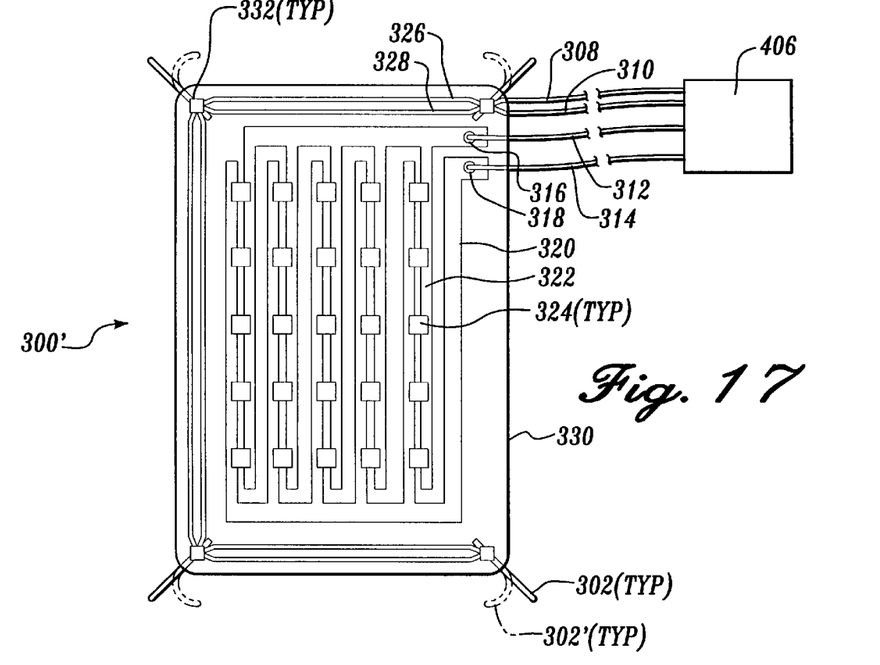
FIG. 17 is a plan view of a quadrilateral sheet-like probe that has four anchors disposed at its corners, showing an electrical heater disposed at each anchor.

Two other similar embodiments of the claimed invention are illustrated in FIGS. 16–17. In FIG. 16, an array 300 is illustrated that includes a plurality of light sources 324; the array is thus adapted to be implanted at a treatment site (not shown) within a patient's body to provide PDT. The light sources 324 are mounted on a flexible substrate 330, which has a generally rectangular shape with rounded corners. Leads 312 and 314 are respectively attached to connectors 316 and 318 on conductive traces 320 and 322. The conductive traces are applied to the surface of substrate 330, and light sources 324 are mounted so that electrical contacts (not shown) on the light sources are electrically coupled to conductive traces 320 and 322. The other ends of leads 312 and 314 are connected to a power supply 406, which provides the electrical current that is carried through leads 312 and 314 and conductive traces 320 and 322 to energize the light sources.

Also connected to power supply 406 are leads 308 and 310. These leads are coupled to conductive traces 326 and 328, which extend around and just inside three edges of substrate 330. Four anchors 302 are positioned so that a each anchor is disposed at a different one of the four corners of the substrate. Anchors 302 are fabricated as elongate bars from an SMA that is electrically and thermally conductive. Each anchor is electrically connected at spaced-apart points 304 and 306 (i.e., spaced apart along the length of the anchor) to conductive traces 326 and 328, respectively. Thus, an electrical current provided by power supply 406 can be selectively conveyed through leads 308 and 310, and by conductive traces 326 and 328, in parallel, through a section 338 of each anchor 302 that extends between points 304 and 306. This electrical current causes resistive heating of the SMA comprising the anchors to a temperature above that required for the shape memory effect to occur. When array 300 is initially implanted at the desired treatment site, which will typically be done endoscopically, electrical current is applied through leads 308 and 310, heating anchors 302 so that they exceed the temperature required for austenite crystal formation and become relatively straight. When straight, anchors 302 do not engage any surrounding tissue in the patient's body. However, after array 300 has been positioned as desired within the patient's body, electrical current flowing through leads 308 and 310 from power supply 406 is interrupted. As electrical current ceases to flow through section 338 of anchors 302, the overall temperature of each anchor 302 decreases and martensite crystals start to form in the molecular structure of the anchor. At the onset of martensite crystal formation, the shape memory effect swiftly causes each anchor 302 to curl (assuming the shape referenced by numeral 302') so that the anchor engages adjacent tissue. When anchors 302' engage the adjacent tissue, array 300 becomes securely fixed inside the patient's body. Next, an electrical current is caused to flow from power supply 406 to light sources 324 so they illuminate the tissue within the patient's body to provide the desired light therapy. After the light therapy is complete, the flow of electrical current from power supply 402 to the light sources is interrupted.

Once the flow of electrical current through section 338 of each anchor is again enabled, anchor 302' will begin to heat, causing the martensite crystals in its molecular structure to break down and austenite crystals to form. At the austenite crystal formation temperature, the shape memory effect causes anchor 302' to quickly straighten and disengage from the adjacent tissue in the patient's body, so that array 300 can be readily removed.

In FIG. 17, an alternative array 300' is illustrated in which leads 308 and 310 are attached to a heater plate 332. Similarly, conductive traces 326 and 328 are coupled to that heater plate, and to three other heater plates 332 disposed at the other three corners of substrate 330. Each of heater plates 332 is mounted in thermal conductive contact with one of the anchors 302, so that an electrical current conveyed through leads 308 and 310 from power supply 406 passes through heater plates 332 in parallel. Electrical current flowing through heater plates 332 generates heat that is conducted into each anchor 302, causing them to assume their relatively straight shape during positioning of the array at the desired treatment site. Further, the selective activation of anchors 302' that causes them to curl and engage adjacent tissue is thus implemented as described above in connection with array 300, by enabling the SMA comprising the anchors to cool below the martensite phase temperature. Similarly, the illumination of tissue at the treatment site by light sources 324 is performed in substantially the same manner as discussed above for array 300. Once the light therapy is complete, the shape memory effect is again used to selectively disengage anchors 302' from the adjacent tissue so that array 300' can be extracted from within the patient's body.

Power supplies 402 and 406 can comprise either a direct current (DC) or an alternating current (AC) source that is preferably disposed inside the patient's body, at another site, but may alternatively comprise an external source. Electromagnetic energy for an internal power supply can be inductively coupled transcutaneously into the patient's body from an external electromagnetic coil and external source and can provide the power required directly, or can be used to charge a storage battery in the internal power supply that is used to provide the required electrical current.

Figure 19:
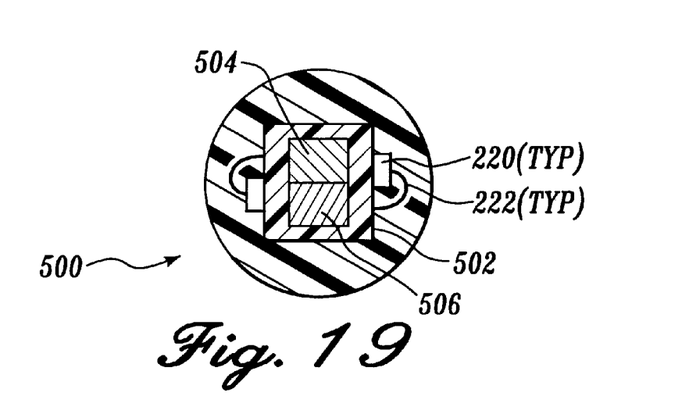
FIG. 19 is a cross-sectional view of a rod-like probe that uses a spring steel strip to distort the probe into a serpentine shape to anchor the probe, and employs an SMA strip to straighten the probe when inserting or withdrawing the probe from a treatment site.
Figures 21, 22, 23:
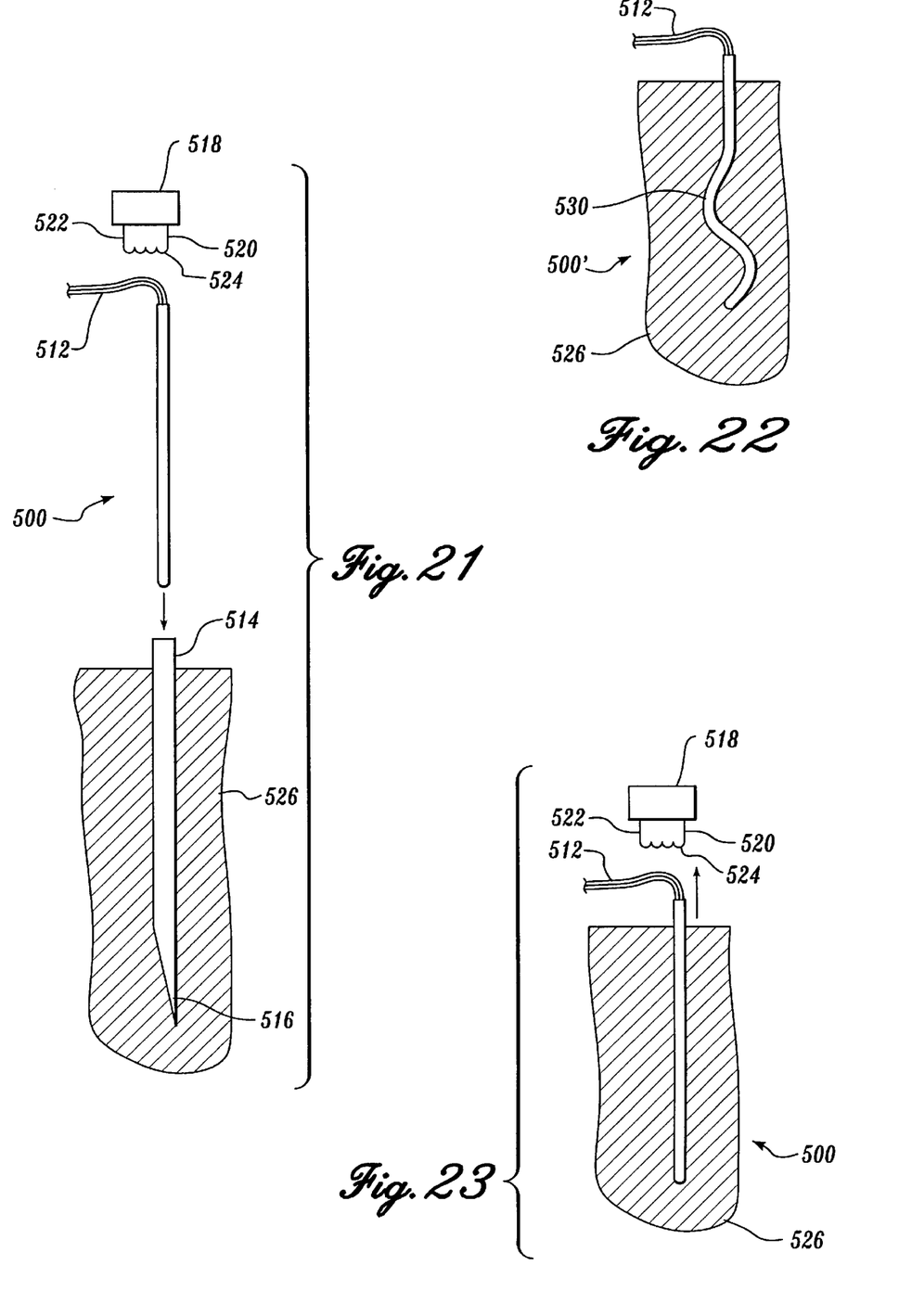
FIG. 21 is a side view showing how induction coil is used to heat the SMA element to straighten the probe of FIG. 19 for insertion through a guide tube, into a treatment site within tissue.
FIG. 22 is a side view of the embodiment of FIGS. 19 and 21, showing the serpentine shape that the probe is forced to adopt in response to the spring force exerted by the spring steel strip within the probe.
FIG. 23 is a side elevational view showing how heat provided by an induction coil causes the SMA element to assume a straight memory shape, thereby straightening the probe so that it can readily be withdrawn.

FIGS. 19 and 21–23 illustrate yet another embodiment of the present invention that is used to maintain a rod-like probe 500 fixed at a treatment site within a patient's body. Referring to FIG. 19, it will be noted that probe 500 includes a flexible substrate 502 on which are mounted a plurality of light emitting devices 220. The flexible substrate extends generally longitudinally through the probe and the light emitting devices (preferably LEDs although virtually any type of light emitting device can instead be used) are mounted on flexible conductive traces (not shown) that are disposed on opposite sides of the flexible substrate. The light emitting devices thus comprise a linear array of spaced apart light sources. Each light emitting device 220 is also connected to another flexible conductive trace (not shown) that extends along the flexible substrate, by fly wires 222. Probe 500 is thus similar in function to probe 200, which was described above. However, extending longitudinally through the interior of flexible substrate 502 along the length of the probe are a strip 504 of SMA, and a strip 506 of a spring steel alloy. Strip 506 has been formed and heat treated to have a normal serpentine disposition 530, as illustrated by the shape of probe 500 in FIG. 22. In contrast, the SMA comprising strip 504 assumes a generally straight memory shape when heated above its austenite phase transition temperature, and has not been trained to have a memory shape associated with the martensite phase of the SMA. When strip 504 straightens, it exerts sufficient force against the elastomeric spring force of strip 506, so that probe 500 changes from the serpentine shape of strip 506, to become substantially straight, as shown in FIG. 21.

Figure 20:
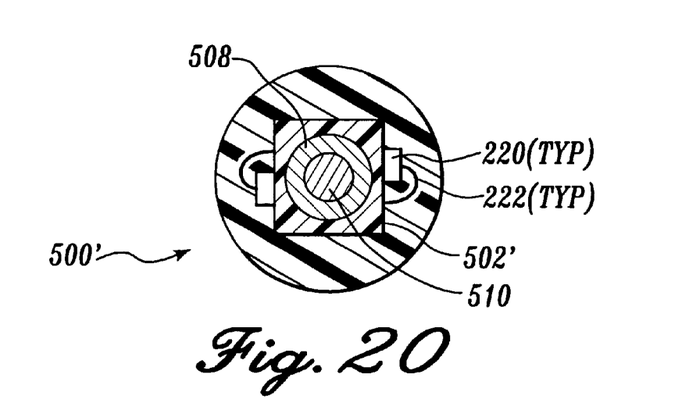
FIG. 20 is a cross-sectional view of an alternative configuration for the embodiment illustrated in FIG. 19, that employs a spring steel core within an SMA tube.

An alternative configuration of this embodiment is a probe 500', which is illustrated in FIG. 20. Probe 500' includes a flexible substrate 502', which extends through much of the longitudinal length of probe 500' (probe 500' is identical to probe 500 in its external appearance). Light emitting devices 220 are spaced apart in linear arrays extending along opposite sides of flexible substrate 502', just as in probe 500. However, instead of strips 504 and 506 being embedded within the flexible substrate, a longitudinally extending tube 508 with an inner core 510 is disposed in the center of flexible substrate 502'. Tube 508 comprises a suitable SMA, while core 510 comprises a spring steel alloy having a normal relaxed serpentine shape that distorts probe 500' to appear like probe 500 in FIG. 22. The memory shape (in its austenite phase) of the SMA comprising tube 508 is generally straight. Thus, when tube 508 is heated above the temperature required for its change from the martensite phase to the austenite phase, tube 508 straightens probe 500', providing sufficient force to overcome the elastomeric spring force of core 510 so that the probe becomes straight (like probe 500 in FIG. 21) rather than serpentine (like probe 500' in FIG. 22).

To heat either strip 504 or tube 508 above the austenite phase temperature so that the SMA straightens into its memory shape, a high-frequency power source 518 is used to produce a high frequency current that is applied through leads 520 and 522 to an induction coil 524, as shown in FIGS. 21 and 23. The induction coil induces eddy currents within strip 504 of probe 500 (or within tube 508 of probe 500') that heat the SMA above its austenite phase temperature point. While thus heated, probes 500/500' are straightened, and as shown in FIG. 21, probe 500 is readily inserted through a guide tube 514 into a treatment site within tissue 526 of the patient. Guide tube 514 has a sharp point 516 that enables it to be readily inserted into the tissue at a desired treatment location.

After probe 500/500' has been inserted into the treatment site within tissue 526 through guide tube 514, the guide tube is withdrawn over the probe and over leads 512. High frequency power source 518 and inductive coil 524 are then de-energized and removed. The distal ends of leads 512 are electrically coupled to the flexible conductors on the flexible substrate within the probe; the other ends (not shown) of the leads are connected to light power supply 402 (shown in FIGS. 6 and 7), which energizes the light emitting devices so that they begin to provide light therapy to the internal treatment site. As the SMA strip (or tube) extending through the probe cools to the martensite phase change temperature, the elastomeric spring force provided by strip 506 in probe 500 or core 510 in probe 500' again causes the probe to assume the serpentine shape shown in FIG. 22, so that the probe is engaged within tissue 526. To remove probe 500/500' after the light therapy (or other medical treatment administered by the probe is completed), high frequency power source 518 is energized, and induction coil 524 is brought into the proximity of the probe so that the SMA comprising strip 504 or tube 508 within the probe is again heated above its austenite phase change temperature, causing the probe to again become straight, as shown in FIG. 23. When straightened by the force of the SMA, the probe is easily withdrawn from tissue 526.

An alternative mode of operation for probe 500/500' is also possible. It should be apparent that the strip (or core) comprising spring steel alloy can have a normal state that is straight, while the strip (or tube) of SMA has a memory shape that is serpentine. For this alternative, the probe is fixed in place when the SMA is heated sufficiently so that it transitions to its memory shape in the austenite phase. Similarly, the probe is withdrawn when the SMA cools sufficiently to transition to its martensite phase so that the spring steel straightens the probe.

It is contemplated that it may be preferable to coat the exterior surface of the medical device and the surface of any embodiments of the present invention in which the anchors are exposed, with a biocompatible coating such as a polymer plastic. While an SMA such as Nitinol is relatively biologically inert, other types of SMA may not be.

It should be noted that the use of a source of thermal energy (e.g., a heated rod) can be used to activate a shape memory change of the SMA elements comprising any form of the present invention instead of an electrical current provided from an electrical power supply. Similarly, an electrical current can be used to provide the heating required to activate the SMA element in any form of the present invention instead of a heat source. It should be apparent that other types of heating and cooling can be employed to cause a change in the shape of an SMA element. For example, a Peltier junction that is thermally linked to the SMA element could be electrically energized to provide either heating or cooling of the SMA. It is also contemplated that the probe to be anchored at a treatment site may be attached to a distal end of a catheter through which a fluid that is heated or cooled to a temperature required to activate a shape memory phase change of an SMA anchor attached to the probe to either engage or disengage the anchor from tissue adjacent the treatment site. The fluid can be circulated to either a heat or cold source module, which for example, uses a Peltier junction to selectively heat or cool the fluid. Alternatively, other types of heating or cooling techniques, such as a liquefied gas source, the expansion of a compressed fluid through an expansion valve, or the condensing of a fluid under pressure can be employed to change the temperature of the fluid circulated into and through the probe.

The above discussion discloses several different embodiments of the present invention in which different shapes are used as anchors that are selectively activated to engage or disengage tissue. However, it should be apparent that many other shapes of SMA can be used to anchor a medical device at a treatment site within a patient's body within the scope of the present invention. For example, a straight section of SMA could be activate to form a spiral shape that engages tissue, thereby anchoring an attached medical device at a treatment site. Furthermore, it is contemplated that the activated state of an anchor in any form of the invention can be reversed from that disclosed in any of the above embodiments, so that while the SMA is in the austenite phase, the anchor can be designed to either engage or not engage the tissue, and when the SMA is cooled to the martensite phase temperature, the anchor will correspondingly either disengage or engages the tissue respectively. It should be apparent that the shape memory effect can be applied to provide for a shape change in either state that serves to anchor the medical device, probe, or array at the treatment site within the patient's body.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for fixing a medical device at a site within a patient's body, comprising the steps of:
   (a) providing an anchor for the medical device, comprising a shape memory metal, said shape memory metal having a first shape associated with a first state and a second shape associated with a second state, and changing from said first state to said second state as a function of temperature;
   (b) inserting the medical device into the patient's body so that it is disposed at the site, said shape memory metal being in said first state while the medical device is positioned at the site; and
   (c) changing the temperature of the shape memory metal so that it transitions from said first state to said second state and thus changes from said first shape to said second shape, said second shape causing engagement of tissue within the patient's body so as to resist movement of the medical device relative to the site in at least one direction, and thus tending to fix the medical device at the site.

2. The method of claim 1, wherein the step of changing the temperature comprises the step of energizing an electrical current to heat the shape memory metal.

3. The method of claim 1, wherein the step of changing the temperature comprises the step of de-energizing an electrical current to enable the shape memory metal to cool.

4. The method of claim 1, wherein the step of changing the temperature comprises the step of applying thermal energy to heat the shape memory metal by heat transfer from a thermal source that is hotter than the shape memory metal.

5. The method of claim 1, wherein the step of changing the temperature comprises the step of transferring thermal energy from the shape memory metal to a thermal sink that is cooler than the shape memory metal to enable the shape memory metal to cool.

6. The method of claim 1, wherein the second shape comprises an expanded loop, and the first shape comprises a collapsed loop.

7. The method of claim 1, wherein the second shape comprises an arcuate hooked element, and the first shape comprises a substantially straight element.

8. The method of claim 1, wherein the second shape comprises a serpentine shaped element, and the first shape comprises a substantially straight element.

9. The method of claim 1, wherein the anchor is disposed substantially against a surface of the medical device when the shape memory metal has the first shape, and when the shape memory metal has the second shape is deflected away from the surface of the medical device, to engage the tissue in the patient's body.

10. The method of claim 1, wherein the anchor further comprises an elastomeric spring element that determines a shape of the medical device in one of the first and second states of the shape memory metal, the shape memory metal determining the shape of the medical device in another of the first and the second states of the shape memory metal, the shape of the medical device determining whether the medical device is fixed at the site.

11. The method of claim 10, wherein the shape memory metal changes the shape of the medical device to engage tissue at the site and the spring element changes the shape of the medical device to disengage the tissue at the site.

12. The method of claim 10, wherein the spring element changes the shape of the medical device to engage tissue at the site and the shape memory metal changes the shape of the medical device to disengage the tissue at the site.

13. The method of claim 1, wherein the step of changing the temperature comprises the step of inducing eddy currents to flow within the shape memory metal to heat it.

14. Apparatus for fixing a medical device al a site within a patient's body, comprising:
(a) a shape memory element that is connected to the medical device, said shape memory element having a first shape associated with a first state and a second shape associated with a second state, and changing from said first state to said second state as a function of a temperature of the shape memory element; and
(b) means for changing the temperature of the shape memory element, causing it to transition from the first state to the second state, one of said first and second shapes being adapted to engage tissue within the patient's body so as to resist movement of the medical device in at least one direction, and thus tending to fix the medical device at the site.

15. The apparatus of claim 14, wherein the shape memory element comprises a loop, said loop being open when the shape memory element is in one of said first and second states, and being closed when the shape memory element is in another of the first and second states.

16. The apparatus of claim 14, wherein the shape memory element comprises an elongate strip, said elongate strip being curved in an arc when the shape memory element is in one of said first and second states, and being substantially straighter when in another of said first and second states.

17. The apparatus of claim 16, wherein an end of the elongate strip penetrates into the tissue adjacent the site when the elongate strip becomes curved in the arc.

18. The apparatus of claim 14, wherein the shape memory element comprises a rod having a distal end that engages the tissue adjacent the site when the shape memory element transitions between the first and second states.

19. The apparatus of claim 14, wherein the shape memory element comprises a section of wire, said section of wire being substantially curved in a serpentine shape when the shape memory element is in one of said first and second states, and being substantially straighter when in the other of said first and second states.

20. The apparatus of claim 14, wherein the shape memory element is disposed generally against a surface of the medical device when in one of the first and second states, and extends substantially away from the surface of the medical device when in another of said first and second states.

21. The apparatus of claim 14, further comprising a biocompatible coating applied to the shape memory element.

22. The apparatus of claim 14, wherein the means for changing the temperature comprise a resistive heating element that produces heat to change the temperature of the shape memory element when the resistive heating element is energized with an electrical current.

23. The apparatus of claim 14, wherein the means for changing the temperature comprise one of a thermal source that is hotter than the shape memory element and conveys thermal energy to the shape memory element to heat the shape memory element, and a thermal sink that is colder than the shape memory element and conducts thermal energy away from the shape memory element to cool the shape memory element.

24. The apparatus of claim 14, further comprising an elastomeric spring element that provides a spring force acting against the shape memory element, said spring element determining one of the first and second shapes, said shape memory element determining another of the first and second shapes, so that one of the spring element and the shape memory element fixes the medical device at the site, and the other of the spring element and the shape memory element causes the medical device to be disengaged from the site, as a result of shape memory element changing between the first and second states.

25. The apparatus of claim 24, wherein the spring element changes a shape of the medical device so that the medical device engages tissue at the site, and the shape memory element changes the shape of the medical device to disengage the medical device from the tissue at the site.

26. The apparatus of claim 24, wherein the shape memory element changes a shape of the medical device so that the medical device engages tissue at the site, and the spring element changes the shape of the medical device to disengage the medical device from the tissue at the site.

27. The apparatus of claim 14, further comprising an inductive coil; and a high frequency power supply coupled to the inductive coil to energize it, said inductive coil comprising the means for changing the temperature of the shape memory element, by inducing eddy currents to circulate within the shape memory element that produce heat.

28. A method for fixing a medical device at an internal treatment site within a patient's body, comprising the steps of:
   (a) providing a selectively actuated anchor for the medical device, said anchor changing between a first shape and a second shape in response to a signal;
   (b) advancing the medical device into the patient's body and to the treatment site while the anchor is in one of the first shape and the second shape; and
   (c) selectively causing the anchor to transition between the first shape and the second shape in response to a state of the signal, one of said first and said second shapes engaging a portion of the patient's body so as to resist movement of the medical device in at least one direction.

29. The method of claim 28, wherein the anchor comprises a shape memory metal that changes between the first shape and the second shape as a function of temperature.

30. The method of claim 28, wherein the signal comprises a thermal energy that is applied to the anchor.

31. The method of claim 30, wherein a thermal element having a temperature different than that of the shape memory metal is employed to change the temperature of the shape memory metal.

32. The method of claim 28, wherein the signal comprises an electrical current that is employed to heat the shape memory metal.

33. The method of claim 28, wherein the anchor has a larger dimension in at least one direction when the anchor assumes the second shape.

34. The method of claim 28, wherein the anchor forms a curve when transitioning to the second shape.

35. The method of claim 28, wherein the anchor is elongate, having an end that engages tissue in the patient's body when the anchor transitions to the second shape.

36. The method of claim 28, further comprising the step of selectively disengaging the anchor with the signal, so that the anchor transitions to the first shape in which the medical device is freely removable from the internal treatment site.

37. The method of claim 28, wherein the anchor changes a shape of the medical device so that the medical device engages the tissue at the internal treatment site.

38. The method of claim 37, wherein said anchor includes a spring element and a shape memory element that changes between a first and a second state, said shape memory element when in one of the first and second states acting to oppose an elastomeric force developed by the spring element.

39. The method of claim 38, wherein one of the shape memory element and the spring element produces the force that causes the medical device to assume the shape that engages the tissue at the internal treatment site.

40. A method for fixing a medical device at a site within a patient's body, comprising the steps of:
   (a) providing an anchor for the medical device, said anchor comprising a shape memory metal, said shape memory metal having a first shape associated with a first state and a second shape associated with a second state, and changing from said first state to said second state as a function of temperature;
   (b) providing an elastomeric spring element that determines a shape of the medical device in one of the first and second states of the shape memory metal, the shape memory metal determining the shape of the medical device in another of the first and the second states of the shape memory metal, the shape of the medical device determining whether the medical device is fixed at the site;
   (c) inserting the medical device into the patient's body so that it is disposed at the site, said shape memory metal being in said first state while the medical device is positioned at the site; and
   (d) changing the temperature of the shape memory metal so that it transitions from said first state to said second state and thus changes from said first shape to said second shape, said second shape causing engagement of tissue within the patient's body so as to resist movement of the medical device relative to the site in at least one direction, and thus tending to fix the medical device at the site.

41. Apparatus for fixing a medical device at a site within a patient's body, comprising:
   (a) a shape memory element that is connected to a medical device, said shape memory element having a first shape associated with a first state and a second shape associated with a second state, and changing from said first state to said second state as a function of a temperature of the shape memory element, said medical device comprising a probe on which a light source is disposed; and
   (b) means for changing the temperature of the shape memory element, causing it to transition from the first state to the second state, one of said first and second shapes engaging tissue within the patient's body so as to resist movement of the medical device in at least one direction, and thus tending to fix the medical device at the site.

42. Apparatus for fixing a medical device at a site within a patient's body, comprising:
   (a) a shape memory element that is connected to a medical device, said shape memory element having a first shape associated with a first state and a second shape associated with a second state, said shape memory element changing from said first state to said second state as a function of a temperature of the shape memory element;
   (b) an elastomeric spring element that provides a spring force acting against the shape memory element, said spring element determining one of the first and second shapes, said shape memory element determining another of the first and second shapes, so that one of the spring element and the shape memory element fixes the medical device at the site, and the other of the spring element and the shape memory element causes the medical device to be disengaged from the site, as a result of shape memory element changing between the first and second states; and
   (c) means for changing the temperature of the shape memory element, causing it to transition from the first state to the second state, one of said first and second shapes engaging tissue within the patient's body so as to resist movement of the medical device in at least one direction, and thus tending to fix the medical device at the site.

43. Apparatus for fixing a medical device at a site within a patient's body, comprising:

(a) a shape memory element that is connected to a medical device, said shape memory element having a first shape associated with a first state and a second shape associated with a second state, and changing from said first state to said second state as a function of a temperature of the shape memory element;

(b) an inductive coil; and (c) a high frequency power supply coupled to the inductive coil to energize it, said inductive coil comprising the means for changing the temperature of the shape memory element, by inducing eddy currents to circulate within the shape memory element that produce heat, causing it to transition from the first state to the second state, one of said first and second shapes engaging tissue within the patient's body so as to resist movement of the medical device in at least one direction, and thus tending to fix the medical device at the site.

* * * * *